(12) United States Patent
Herwig et al.

(10) Patent No.: US 6,222,073 B1
(45) Date of Patent: Apr. 24, 2001

(54) CATALYTIC SYNTHESIS OF N-ALKYLATED ANILINES FROM OLEFINS AND ANILINES

(75) Inventors: Jürgen Herwig, Hünxe; Matthias Beller, Rostock; Claudia Breindl; Harald Trauthwein, both of München; Elisabeth Eichberger; Anton Eichberger, both of Passau, all of (DE)

(73) Assignee: Aventis Research & Technologies GmbH & Co. KG (DE)

( * ) Notice: Subject to any disclaimer, the term of this patent is extended or adjusted under 35 U.S.C. 154(b) by 0 days.

(21) Appl. No.: 09/600,267

(22) PCT Filed: Dec. 19, 1998

(86) PCT No.: PCT/EP98/08343

§ 371 Date: Jul. 13, 2000

§ 102(e) Date: Jul. 13, 2000

(87) PCT Pub. No.: WO99/36388

PCT Pub. Date: Jul. 22, 1999

(30) Foreign Application Priority Data

Jan. 17, 1998 (DE) .............................................. 198 01 598

(51) Int. Cl.⁷ .................................................. C07C 209/00
(52) U.S. Cl. .......................... 564/395; 564/399; 564/404; 564/405
(58) Field of Search .................................... 564/395, 404, 564/405, 399

(56) References Cited

FOREIGN PATENT DOCUMENTS 0598962 6/1994 (EP) .
0814075 12/1997 (EP) .

OTHER PUBLICATIONS

Arnauld, T., et al, *Tetrahedron* 53:4137–4144, "The Chemistry of Pentavalent Organobismuth Reagents. Part 14. Recent Advances in the Copper–Catalyzed Phenylation of Amines". (1997).

*Primary Examiner*—Samuel Barts
(74) *Attorney, Agent, or Firm*—Connolly Bove Lodge & Hutz LLP

(57) ABSTRACT

Process for the preparation of an N-arylethylaniline of the formula (I)

$$Ar-N(R^1)_{2-n}(CHR^2CHR^3Ar')_n \qquad (I)$$

by reacting an aromatic olefin of the formula (II)

$$Ar'CR^3=CHR^2 \qquad (II)$$

with an aniline of the formula (III)

$$Ar-N(R^1)_{2-n}(H)_n \qquad (III)$$

in an inert solvent in the presence of at least one basic catalyst selected from the group consisting of alkali metal alcoholates and alkaline earth metal alcoholates or alkali metal amides and alkaline earth metal amides, where, in the formulae (I) to (III), Ar and Ar', independently of one another, are an aryl radical selected from the group consisting of the fused and nonfused $C_6$–$C_{22}$-aromatics and of the fused or nonfused $C_5$-$C_{22}$heteroaromatics which have at least one nitrogen, oxygen or sulfur atom in the ring;

$R_1$, $R_2$ and $R_3$, independently of one another, are a hydrogen atom, a $C_1$–$C_8$-alkyl radical or an aryl radical Ar; and n is the number 1 or 2.

15 Claims, No Drawings

US 6,222,073 B1

CATALYTIC SYNTHESIS OF N-ALKYLATED ANILINES FROM OLEFINS AND ANILINES

This application is a 371 of PCT/EP98/08343 filed Dec. 19, 1998.

DESCRIPTION

The present invention relates to a novel process for the preparation of N-alkylated anilines.

Substituted anilines are of industrial importance as precursors for dyes, fine chemicals, pharmaceuticals and agrochemical products. In this context, N-alkylated anilines are also industrially important. The preparation of substituted N-alkylated anilines is carried out industrially essentially by nitration of a corresponding aromatic, subsequent hydrogenation and alkylation by means of alkyl halides (e.g. methyl iodide) or alkyl sulfates. In all known alkylations of anilines, stoichiometric amounts of salt byproducts are therefore obtained, which is ecologically disadvantageous. In addition, the alkylations with functionalized alkyl halides, such as, for example, arylethyl bromides, take place with insufficient selectivity, so that further byproducts are formed.

It is the object of the present invention to provide a process for the preparation of substituted, N-alkylated anilines from simple starting materials under mild reaction conditions, which can be carried out on an industrial scale and in which no salt byproducts are obtained.

This object is achieved by a process for the preparation of an N-arylethylaniline of the formula (I)

  (I)

by reacting an aromatic olefin of the formula (II)

  (II)

with an aniline of the formula (III)

  (III)

in an inert solvent in the presence of at least one basic catalyst selected from the group consisting of alkali metal alcoholates and alkaline earth metal alcoholates or alkali metal amides and alkaline earth metal amides, where, in the formulae (I) to (III), Ar and Ar', independently of one another, are an aryl radical selected from the group consisting of the fused and nonfused $C_6$–$C_{22}$-aromatics and of the fused or nonfused $C_5$–$C_{22}$heteroaromatics which have at least one nitrogen, oxygen or sulfur atom in the ring;

$R_1$, $R_2$ and $R_3$, independently of one another, are a hydrogen atom, a $C_1$–$C_8$-alkyl radical or an aryl radical Ar; and n is the number 1 or 2.

The process according to the invention is particularly suitable for reacting primary aromatic amines and secondary aliphatic and aromatic amines.

Furthermore, it is possible for the N-arylethylaniline of the formula (I), in an extension of the intermolecular coupling between the aromatic olefin of the formula (II) and the aniline of the formula (III), to be prepared by an intramolecular amination of a corresponding compound.

An important property of the process according to the invention is that the anilines for the first time react with styrenes under base catalysis, generally with good to very good yields of from 70 to 99%. Salt byproducts are not formed here.

Examples of the aryl radical Ar are phenyl, naphthyl, anthryl, phenanthryl and biphenyl, pyridyl, furfuryl or pyrazolyl radicals.

The inert solvent can be selected from the group consisting of aromatic hydrocarbons, such as toluene, xylenes, anisole and tetralin, and aliphatic ethers, such as tetrahydrofuran, dimethoxyethane, dioxane, tetrahydropyran and formaldehyde acetals.

According to a preferred embodiment of the invention, the basic catalyst is selected from the group consisting of the tert-butanolates, methanolates, propanolates and 2-ethylhexanolates of the alkali metals and alkaline earth metals, in particular from the corresponding potassium and sodium ompounds. Examples of these are potassium tert-butanolate, potassium methanolate, potassium ethanolate, potassium propanolate, potassium isopropanolate, potassium 2-ethylhexanolate, potassium phenolate and potassium 2-amino-1-methanolate.

Potassium tert-butanolate is particularly preferred here.

In a further, likewise preferred embodiment according to the invention, the basic catalyst is selected from the amides, dimethylamides, diisopropylamides and anilides of the alkali metals and alkaline earth metals, in particular their potassium and sodium compounds.

Examples of these are potassium amide, potassium dimethylamide, potassium diisopropylamide and potassium anilide.

It is also possible to use, as basic catalyst, a mixture of at least two of the basic catalysts described above.

The catalyst can be used directly in the form of one of said compounds or similar compounds. However, it is sometimes advantageous to prepare the active compound in situ from suitable precursors, owing to the stability of the basic catalyst.

The basic catalyst can be used in an amount of from 0.01 to 20 mol %, in particular from 0.1 to 5 mol %, based on the aniline of the formula (III).

The aryl radicals Ar or Ar' in the formulae (I) to (III) can, independently of one another, have up to 8 substituents which are identical or different and are a hydrogen, fluorine, chlorine, bromine or iodine atom or a $C_1$–$C_8$-alkyl, $C_1$–$C_8$-alkoxy, $C_1$–$C_8$-acyloxy, HO, $O_2$N, CN, HOC(O), HC(O), HOS($O_2$), $R^4S(O)_2$, $R^4S(O)$, $H_2N$, $R^4N(H)$, $R^4{}_2N$, $R^4C(O)$ N(H), $R^4C(O)$, (OCH)HN, Ar"C(O), ArC(O)O, $CF_3$, $H_2NC$ (O), $R^4OC(O)C(H)=C(H)$, Ar"$_2$P(O), $R^4{}_2P(O)$ or $R^4{}_3$Si radical or a heteroaryl radical having 5 or 6 atoms in the aryl ring, R being a $C_1$–$C_{12}$-alkyl radical and Ar" being selected from the group consisting of the fused or nonfused $C_6$–$C_{22}$-aromatics and of the fused or nonfused $C_5$–$C_{22}$-heteroaromatics which have at least one nitrogen, oxygen or sulfur atom in the ring.

The reaction takes place at temperatures of from 0 to 200° C., in particular at from 10 to 150° C. and preferably at from 20 to 120° C.

In the case of some aromatic olefins of the formula (II), it may be advantageous, owing to the tendency toward secondary oligomerization and polymerization reactions, to add a polymerization inhibitor. The conventional polymerization inhibitors may be used for this purpose, such as, for example, p-quinone.

The following examples serve merely to illustrate the process.

EXAMPLES

General

All reactions are carried out in the absence of air and water under an argon atmosphere in a 30 ml pressure tube from Aldrich, having a Teflon seal. The solvents used were dried by conventional methods known from the literature and were stored over a 4 Å molecular sieve under an argon atmosphere. All starting materials were dried before use and likewise stored over a 4 Å molecular sieve and under an inert gas. $^1$H-NMR (400 MHz) and $^{13}$C-NMR spectra (100 MHz) are calibrated by means of the shifts of the solvents used.
General Working Method (GWM Below):

1.1 mmol of potassium tert-butylate KOtBu (=123 mg=10 mol %) are initially introduced into a pressure tube thoroughly heated and flushed with argon, 100 µl of hexadecane (internal standard) are added and the solid is suspended in 4 ml of THF. 0.011 mol of olefin and 0.011 mol of amine are added in succession under an argon stream, the solution becoming strongly colored (yellow to violet). Before the reaction mixture is heated to 120° C. for 20 h in an oil bath, stirring is carried out for a further 15 min at ambient temperature. During the reaction, the color of the reaction solution becomes more intense. After cooling, the mixture is hydrolyzed with 5 ml of water, during which virtually complete decolorization of the solution occurs. The mixture is then mixed with 20 ml of 1 M hydrochloric acid and 10 ml of methylene chloride. The acidic, aqueous phase is separated off in a separating funnel, and the organic phase is extracted three times more with 15 ml of 1 M hydrochloric acid each time. Thereafter, the combined aqueous phases are neutralized with sodium carbonate and extracted five times with 15 ml of methylene chloride each time, and the organic phases are rinsed several times with water. After drying of the organic phase over magnesium sulfate, the solvent is removed in vacuo. The liquid products are isolated by column chromatography.

Example 1

According to GWM, 0.011 mol (=1.00 ml) of aniline and 0.011 mol (=1.25 ml) of styrene are reacted with one another. The product is isolated by column chromatography using ethyl acetate/n-hexane (1:3) as eluent, the product N-phenylethylaniline being obtained as a yellow liquid.
Yield: 78% of theory
Molecular weight: 197.28 g/mol
Rf value: 0.71 (hexane/ethyl acetate 3:1)
$^1$H-NMR (400 MHz, CDCk$_3$, 25° C.): δ =2.93 (t, 2H, J=7.03 Hz, —NH—CH$_2$—CH$_2$—), 3.42 (t, 2H, J=7.03 Hz, —NH—CH$_2$—), 3.69 (s, 1H, —NH—), 6.62 (d, 2H, J=8.05 Hz, o-aniline-H), 6.71 (t, 1H, J=7.03 Hz, p-aniline-H), 7.15–7.35 (m, 7H).
$^{13}$C-NMR (400 MHz, CDCl$_3$, 25° C.): δ =35.5 (—NH—CH$_2$—), 45.0 (—NH—CH$_2$CH$_2$), 113.0 (o-aniline-C), 117.4 (p-aniline-C), 126.4 (m-aniline-C), 128.6 (o-phenyl-C), 128.8 (p-phenyl-C), 129.4 (m-phenyl-C), 139.3 (quart. C-aniline).
GC-MS: m/e=197 [M$^+$], 10$^6$ [M$^+$-CH$_2$-phenyl], 91, 77, 65.

Example 2

According to GWM, 0.011 mol (=1.20 ml) of N-methylaniline and 0.011 mol (=1.00 ml) of styrene are reacted with one another. The product is isolated by column chromatography using ethyl acetate/n-hexane (1:3) as eluent, the product N-methyl-N-phenylethylaniline being obtained as a yellow liquid.
Yield: 53% of theory
Molecular weight: 211.3i g/mol
GC-MS: m/e =211 [M$^+$], 120 [M$^+$-CH$_2$-phenyl], 104, 91, 77, 51, 28.

Example 3

According to GWM, 0.011 mol (=1.00 ml) of aniline and 0.011 mol (=1.45 ml) of 3-methylstyrene are reacted with one another. The product is isolated by column chromatography using ethyl acetate/n-hexane (1:5) as eluent, the product N-2-[(3-tolyl)ethyl]aniline being obtained as a pale yellow liquid.
Yield: 90% of theory
Molecular weight: 211.31 g/mol
R$_f$ value: 0.51 (hexane/ethyl acetate 5:1)
$^1$H-NMR (400 MHz, CDCl$_3$, 25° C.): δ =2.39 (s, 3H, —CH$_3$), 2.92 (t, 2H, J=7.03 Hz, —NH—CH$_2$—CH$_2$—), 3.44 (t, 2H, J=7.03 Hz, —NH—CH$_2$—), 3.69 (s, 1H, —NH—), 6.64 (d, 2H, J=8.05 Hz, o-aniline-H), 6.75 (t, 1H, J=7.50 Hz, paniline-H), 7.04–7.12 (m, 3H), 7.17–7.31 (m, 3H).
$^{13}$C-NMR (400 MHz, CDCl$_3$, 25° C.): δ=21.4 (—CH$_3$), 35.4 (—NH–CH$_2$—), 45.0 (—NH—CH$_2$—CH$_2$—), 112.9 (o-aniline-C), 117.4 (p-aniline-C), 125.7 (m-aniline-C), 127.1, 128.4, 129.2, 129.5, 138.2 (quart. C—CH$_3$), 139.2 (quart C-phenyl), 148.0 (quart. C-aniline).
GC-MS: m/e=211 [M$^+$], 10$^6$ [M$^+$-CH$_2$-m-tolyl], 77, 51, 28.

Example 4

According to GWM, 0.011 mol (=1.00 ml) of aniline and 0.011 mol (=1.40 ml) of 4-chlorostyrene are reacted with one another. The product is isolated by column chromatography using ethyl acetate/n-hexane (1:5) as eluent, the product N-2-[(4-chlorophenyl)ethyl]aniline being obtained as a yellowish brown liquid.
Yield: 72% of theory
Molecular weight: 231.73 g/mol
R$_f$ value: 0.48 (hexane/ethyl acetate 5:1)
$^1$H-NMR (400 MHz, CDCl$_3$, 25° C.): δ=2.84 (t, 2H, J=7.03 Hz, —NH—CH$_2$CH$_2$—), 3.34 (t, 2H, J=7.03 Hz, —NH—CH$_2$—), 3.61 (s, 1H, —NH—), 6.57 (d, 2H, J=7.50 Hz, o-aniline-H), 6.69 (t, 1H, J=7.50 Hz, p-aniline-H), 7.05–7.27 (m, 6H).
$^{13}$C-NMR (400 MHz, CDCl$_3$, 25° C.): δ=34.7 (—NH—CH$_2$—), 44.8 (—NH—CH$_2$CH$_2$—), 112.9 (o-aniline-C), 117.5 (p-aniline-C), 128.6, 129.2, 130.0, 132.1 (quart. C—Cl), 137.7 (quart. C-phenyl), 147.7 (quart. C-aniline).
GC-MS: m/e=231 [M$^+$], 125 [M$^+$-CH$_2$—NH—phenyl], 106 [M$^+$-CH$_2$chlorophenyl], 89, 77, 63, 51, 28.

Example 5

According to GWM, 0.011 mol (=1.10 ml) of p-fluoroaniline and 0.011 mol (=1.25 ml) of styrene are reacted with one another. The product is isolated by column chromatography using ethyl acetate/n-hexane (1:1) as eluent, the product N-(2-phenylethyl)-(p-fluoro)aniline being obtained as brown liquid.
Yield: 84% of theory
Molecular weight: 215.27 g/mol
R$_f$ value: 0.90 (hexane/ethyl acetate 1:1)
$^1$H-NMR (400 MHz, CDCl$_3$, 25° C.): δ=2.79 (t, 2H, J=7.03 Hz, —NH—CH$_2$CH$_2$—), 3.23 (t, 2H, J=7.03 Hz, —NH—CH$_2$—), 3.42 (s, 1H, —NH—), 6.45–6.50 (m, 2H, o-aniline-H), 6.72–6.83 (m, 2H, m-aniline-H), 7.07–7.29 (m, 5H).
$^{13}$C-NMR (400 MHz, CDCl$_3$, 25° C.): δ=35.4 (—NH—CH$_2$—), 45.6 (—NH—CH$_2$CH$_2$—), 113.7–113.8 (d, J=8 Hz, o-aniline-C), 115.5–115.7 (d, J=22 Hz, maniline-C), 126.1, 128.4, 128.8, 139.1 (quart. C-phenyl), 144.3 (quart. C-aniline), 154.6–156.9 (d, J=235 Hz, quart. C—F).
GC-MS: m/e=215 [M$^+$], 124 [M$^+$-CH$_2$-phenyl], 95, 75, 28.

Example 6

According to GWM, 0.011 mol (=1.25 ml) of o-anisidine and 0.011 mol (=1.25 ml) of styrene are reacted with one another. The product is isolated by column chromatography using ethyl acetate/n-hexane (1:5) as eluent, the product N-(2-phenylethyl)-(o-methoxy)aniline being obtained as a slightly pink liquid.
Yield: 85% of theory
Molecular weight: 227.31 g/mol
$R_f$ value: 0.48 (hexane/ethyl acetate 5:1)
$^1$H-NMR (400 MHz, CDCl$_3$, 25° C.): δ=2.92 (t, 2H, J=7.03 Hz, —NH—CH$_2$CH$_2$—), 3.40 (t, 2H, J=7.03 Hz, —NH—CH$_2$—), 3.80 (s, 3H, —O—CH$_3$), 4.33 (s, 1H, —NH—), 6.68 (t, 2H, J=7.50 Hz), 6.79 (d, 1H, J=6.03 Hz), 6.89 (t, 1H, J=7.50 Hz), 7.18–7.33 (m, 5H).
$^{13}$C-NMR (400 MHz, CDCl$_3$, 25° C.): δ=35.6 (—NH—CH$_2$—), 45.0 (—NH—CH$_2$CH$_2$—), 55.4 (—CH$_3$), 109.5, 109.9, 116.4, 121.3, 126.3, 128.5, 128.7, 138.0 (quart. C—OCH$_3$), 139.5 (quart. C-phenyl), 146.9 (quart. C-aniline).
GC-MS: m/e=227 [M$^+$+], 136 [M$^+$-CH$_2$-phenyl], 121 [M$^+$-CH$_3$—CH$_2$-phenyl], 91, 77,51,28.

Example 7

According to GWM, 0.011 mol (=1.00 ml) of aniline and 0.011 mol (=1.43 ml) of α-methylstyrene are reacted with one another. The product is isolated by column chromatography using ethyl acetate/n-hexane (1:5) as eluent, the product (±)-N-1-(2-phenylpropyl)aniline being obtained as a slightly pink liquid.
Yield: 34% of theory
Molecular weight: 211.31 g/mol
$R_f$ value: 0.63 (hexane/ethyl acetate 5:1)
$^1$H-NMR (400 MHz, CDCl$_3$, 25° C.): δ=1.30 (d, 3H, J=7.03 Hz, —CH$_3$), 3.05 (sextet, 1H, J=7.03 Hz, —CH$_2$—CH—CH$_3$), 3.23 (dd, 1H, J=12.00 Hz, J=8.04 Hz, —CH$_2$—CH—CH$_3$), 3.31 (dd, 1H, J=12.00 Hz, J=8.03 Hz, —CH$_2$—CH—CH$_3$), 3.50 (s, 1H, —NH—); 6.55 (d, 2H, J=8.04 Hz, o-aniline-H), 6.67 (t, 1H, J=7.03 Hz, p-aniline-H), 7.09–7.33 (m, 7H).
$^3$C-NMR (400 MHz, CDCl$_3$, 25° C.): δ=19.7 (—CH$_3$), 39.2 (—NH—CH$_2$—), 50.9 (—NH—CH$_2$—CH—), 112.9 (o-aniline-C), 117.3 (p-aniline-C), 126.6 (m-aniline-C), 127.2, 128.6, 129.2, 144.5 (quart. C-phenyl), 148.1 (quart. C-aniline).
GC-MS: m/e=211 [M$^+$], 106 [M$^+$-CH(CH$_3$)-phenyl], 79,77,51, 28.

Example 8

According to GWM, 0.011 mol (=1.00 ml) of aniline and 0.011 mol (=1.43 ml) of β-methylstyrene are reacted with one another. The product is isolated by column chromatography using ethyl acetate/n-hexane (1:10) as eluent, the product (±)-N-(1-methyl-2-phenylethyl)aniline being obtained as a slightly pink liquid.
Yield: 50% of theory
Molecular weight: 211.31 g/mol
$R_f$ value: 0.37 (hexane/ethyl acetate 10:1)
$^1$H-NMR (400 MHz, CDCl$_3$, 25° C.): δ=1.06 (d, 3H, J=6.50 Hz, CH$_3$), 2.60 (dd, 1H, J=13.50 Hz, J=7.50 Hz, —NH—CH—CH$_2$—), 2.86 (dd, 1H, J=13.50 Hz, J=5.00 Hz, —NH—CH—CH$_2$—), 3.42 (s, 1H, —NH—); 3.68 (sextet, 1H, J=6.50 Hz, —NH—CH—), 6.55 (d, 2H, J=8.02 Hz, o-aniline-H), 6.62 (t, 1H, J=7.03 Hz, p-aniline-H), 7.06–7.25 (m, 7H).
$^{13}$C-NMR (400 MHz, CDCl$_3$, 25° C.): δ=20.2 (—CH$_3$), 42.3 (—NH—CH—), 49.3 (—NH—CH—CH$_2$—), 113.3 (o-aniline-C), 117.2 (p-aniline-C), 126.2 (m-aniline-C), 128.3, 129.3, 138.5 (quart. C-phenyl), 147.2 (quart. C-aniline).

GC-MS: m/e =211 [M$^+$], 120 [M$^+$-CH$_2$-phenyl], 91, 77, 28.

What is claimed is:

1. A process for the preparation of an N-arylethylaniline of the formula (I)

$$Ar\!-\!N(R^1)_{2-n}(CHR^2CHR^3Ar')_n \qquad (I)$$

which comprises reacting an aromatic olefin of the formula (II)

$$Ar'CR^3\!=\!CHR^2 \qquad (II)$$

with an aniline of the formula (III)

$$Ar\!-\!N(R^1)_{2-n}(H)_n \qquad (III)$$

in an inert solvent in the presence of at least one basic catalyst selected from the group consisting of alkali metal alcoholates, alkaline earth metal alcoholates, alkali metal amides and alkaline earth metal amides, where, in the formulae (I) to (III), Ar and Ar', independently of one another, are an aryl radical selected from the group consisting of a fused $C_6$–$C_{22}$-aromatic, a nonfused $C_6$–$C_{22}$-aromatic, a fused $C_5$–$C_{22}$-heteroaromatic and a nonfused $C_5$–$C_{22}$–$C_5$–$C_{22}$-heteroaromatic and wherein the fused and non-fused $C_5$–$C_{22}$-heteroaromatic contains at least one nitrogen, oxygen or sulfur atom in the ring;

$R^1$, $R_2$ and $R_3$, independently of one another, are a hydrogen atom, a $C_1$–$C_8$-alkyl, radical or an aryl radical Ar; and n is the number 1 or 2.

2. The process as claimed in claim 1, wherein the basic catalyst is selected from the group consisting of the tert-butanolate, methanolate, propanolate, 2-ethylhexanolate of the alkali metal and 2-ethylhexanolate of the alkaline earth metals.

3. The process as claimed in claim 2, wherein the basic catalyst is potassium tert-butanolate.

4. The process as claimed in claim 1, wherein the basic catalyst is dimethylamide, diisopropylamide, anilide of the alkali metals or anilide of alkaline earth metals.

5. The process as claimed in claim 1, wherein a mixture of at least two basic catalysts is used.

6. The process as claimed in claim 1, wherein the basic catalyst is used in an amount of from 0.01 to 20 mol % based on the aniline of the formula (III).

7. The process as claimed in claim 1, wherein the aryl radicals Ar or Ar', independently of one another, have up to 8 substituents which are identical or different and are a hydrogen atom, fluorine atom, chlorine atom, bromine atom iodine atom, a $C_1$–$C_8$-alkyl, $C_1$–$C_8$-alkoxy, $C_1$–$C_8$-acyloxy, HO, O$_2$N, CN, HOC(O), HC(O), HOS(O)$_2$, R$^4$S(O)$_2$, R$^4$S (O), H$_2$N, R$^4$N(H), R$^4{}_2$N, R$^4$C(O)N(H) R$^4$C(O), (OCH)HN, Ar"C(O), ArC(O)O, CF$_3$, H$_2$NC(O), R$^4$OC(O)C(H)=C(H), Ar"$_2$P(O), R$^4{}_2$P(O), R$^4{}_3$Si radical or a heteroaryl radical having 5 or 6 atoms in the aryl ring, R$^4$ being a $C_1$–$C_{12}$-alkyl radical and Ar" being selected from the group consisting of the fused $C_6$–$C_{22}$-aromatic, nonfused $C_6$–$C_{22}C_6$–$C_{22}$-aromatic fused $C_5$–$C_{22}$-heteroaromatic and nonfused $C_5$–$C_{22}$–$C_5$–$C_{22}$-heteroaromatic wherein the fused and non-fused $C_5$–$C_{22}$-heteroaromatic contain at least one nitrogen, oxygen or sulfur atom in the ring.

8. The process as claimed in claim 2, wherein the basic catalyst is 2-ethylhexanolate of potassium or sodium compound.

9. The process as claimed in claim 4, wherein the basic catalyst is an anilide of potassium or sodium compound.

10. The process as claimed in claim 9, wherein the basic catalyst is used in an amount from 0.1 to 5 mol % based on the aniline of the formula (III).

11. The process as claimed in claim 8, wherein the basic catalyst is used in an amount from 0.1 to 5 mol % based on the aniline of the formula (III).

12. The process as claimed in claim 11, wherein the aryl radicals Ar or Ar', independently of one another, have up to 8 substituents which are identical or different and are a hydrogen atom, fluorine atom, chlorine atom, bromine atom, iodine atom, a $C_1$–$C_8$-alkyl, $C_1$–$C_8$-alkoxy, $C_1$–$C_8$-acyloxy, HO, $O_2N$, CN, HOC(O), HC(O), HOS(O)$_2$, $R^4S(O)_2$, $R^4S(O)$, $H_2N$, $R^4N(H)$, $R^4{}_2N$, $R^4C(O)N(H)$, $R^4C(o)$, (OCH)HN, Ar"C(O), ArC(O)O, $CF_3$, $H_2NC(O)$, $R^4OC(O)C(H)=C(H)$, Ar"$_2$P(O), $R^4{}_2P(O)$, $R^4{}_3Si$ radical or a heteroaryl radical having 5 or 6 atoms in the aryl ring, $R^4$ being a $C_1$—$C_{12}$-alkyl radical and Ar" being selected from the group consisting of the fused $C_6$–$C_{22}$-aromatic, nonfused $C_6$–$C_{22}$-aromatic fused $C_5$–$C_{22}$-heteroaromatic and nonfused $C_5$–$C_{22}$–$C_5$–$C_{22}$-heteroaromatic wherein the fused and nonfused $C_5$–$C_{22}$-heteroaromatic contain at least one nitrogen, oxygen or sulfur atom in the ring.

13. The process as claimed in claim 1, wherein the reaction takes place at a temperature from 0 to 200° C.

14. The process as claimed in claim 11, wherein the reaction takes place at a temperature from 110 to 150° C.

15. The process as claimed in claim 12, wherein the reaction takes place at a temperature from 20 to 120° C.

* * * * *